United States Patent
Klingenbeck-Regn

(10) Patent No.: US 7,809,106 B2
(45) Date of Patent: Oct. 5, 2010

(54) MEDICAL DIAGNOSTIC SYSTEM AND METHOD FOR CAPTURING MEDICAL IMAGE INFORMATION

(75) Inventor: Klaus Klingenbeck-Regn, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 238 days.

(21) Appl. No.: 11/888,206

(22) Filed: Jul. 31, 2007

(65) Prior Publication Data
US 2009/0016488 A1 Jan. 15, 2009

(30) Foreign Application Priority Data
Aug. 4, 2006 (DE) .................. 10 2006 036 571

(51) Int. Cl.
*G01N 23/04* (2006.01)
(52) U.S. Cl. ........................... 378/63; 378/197
(58) Field of Classification Search ............. 378/37, 378/193–199, 62, 4
See application file for complete search history.

(56) References Cited

U.S. PATENT DOCUMENTS

| | | | |
|---|---|---|---|
| 5,226,066 A | 7/1993 | Barr | |
| 5,452,338 A * | 9/1995 | Granfors et al. | 378/98.11 |
| 5,965,891 A * | 10/1999 | Weinberg | 250/363.02 |
| 6,670,614 B1 | 12/2003 | Plut et al. | |
| 2004/0066906 A1 | 4/2004 | Hornegger et al. | |
| 2005/0027193 A1 | 2/2005 | Mitschke et al. | |
| 2005/0187424 A1 | 8/2005 | Hambuchen et al. | |
| 2007/0102645 A1* | 5/2007 | Maschke | 250/370.09 |

FOREIGN PATENT DOCUMENTS

| | | |
|---|---|---|
| DE | 44 36 828 | 3/1996 |
| DE | 10241184 A1 | 4/2004 |
| DE | 103 23 008 A1 | 12/2004 |
| EP | 1547540 A1 | 6/2005 |

OTHER PUBLICATIONS

Süssner, Pressereferat Medical Solutions "Symbia S—einfach aufrüstbar—Die Symbia-Produktfamilie für True Point SPECT-CT bekommt Zuwachs", Dec. 12, 2005, www.innovations-report.de/specials/printa.php?id=52745.

* cited by examiner

*Primary Examiner*—Hoon Song

(57) ABSTRACT

The invention relates to a medical diagnostic system having two C-arms which are adjustable with the aid of two drive means and serve as retaining devices for one medical measuring system in each case. At least one evaluation unit and at least one display element are provided for each medical measuring system. The first measuring system is an X-ray measuring system comprising an X-ray emitter and an X-ray detector and has a high spatial resolution. The second measuring system is a nuclear medicine measuring system for visualizing tissue functions. Accurate and rapid medical diagnoses and interventions are possible based on image information generated by both measuring systems.

20 Claims, 1 Drawing Sheet

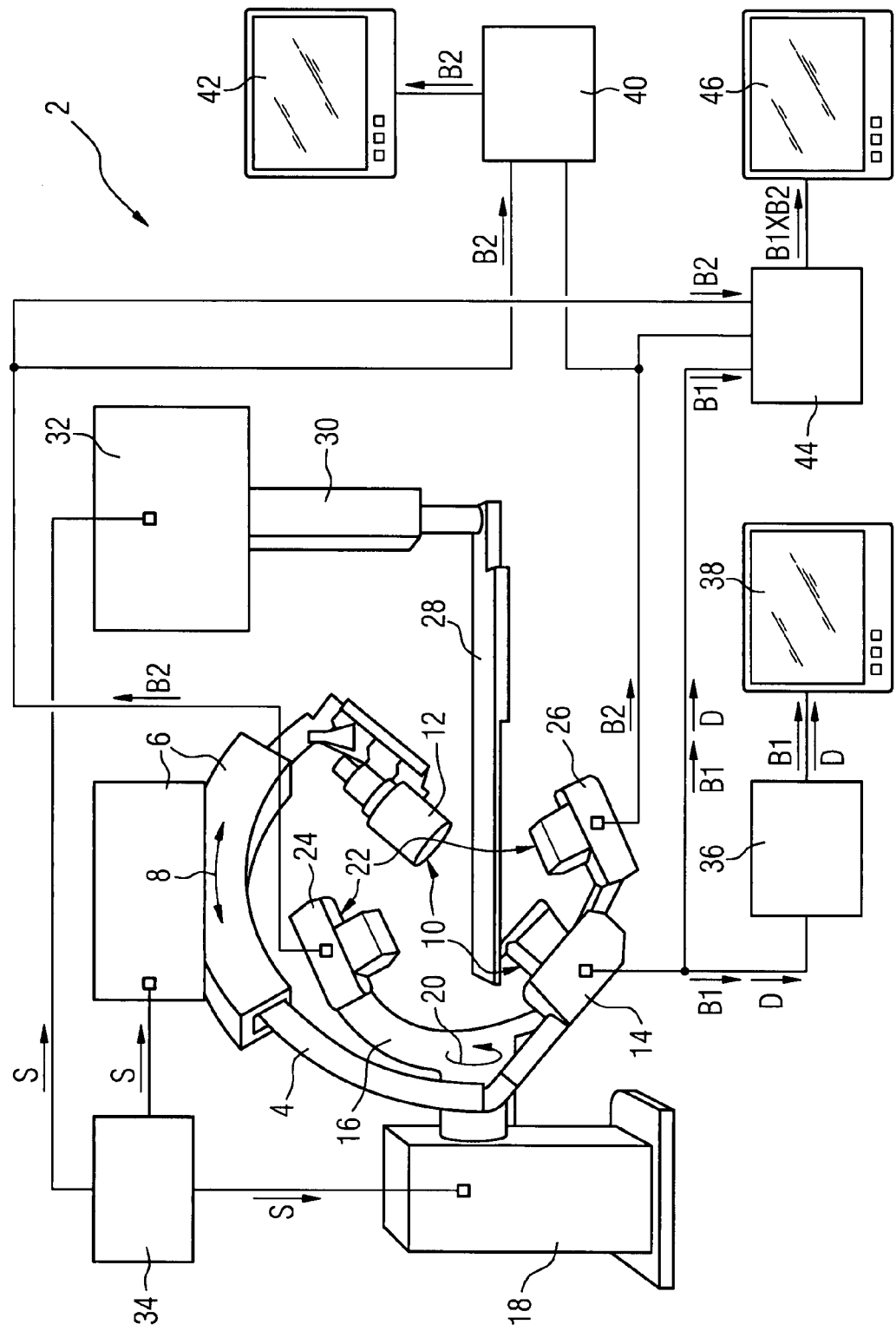

MEDICAL DIAGNOSTIC SYSTEM AND METHOD FOR CAPTURING MEDICAL IMAGE INFORMATION

CROSS REFERENCE TO RELATED APPLICATIONS

This application claims priority of German application No. 10 2006 036 571.2 filed Aug. 4, 2006, which is incorporated by reference herein in its entirety.

FIELD OF THE INVENTION

The invention relates to a medical diagnostic system having two C-arms which are adjustable with the aid of two drive means and serve as retaining devices for one medical measuring system in each case, as well as to a method for capturing medical image information.

BACKGROUND OF THE INVENTION

An X-ray diagnostic apparatus having two C-arms is described in DE 44 36 828 C1. In this arrangement there are disposed at the ends of the first C-arm an X-ray source and an X-ray detector which together form an X-ray measuring system. The first C-arm is in this case supported by a second C-arm which is provided for the purpose of achieving a better spatial positioning of the X-ray measuring system.

U.S. Pat. No. 5,226,066 discloses an X-ray system which has two X-ray measuring apparatuses for simultaneously recording one and the same region of the body from two different perspectives.

An X-ray diagnostic device having a C-arm is known from DE 103 23 008 A1. In this arrangement three-dimensional image information of a bodily region is captured by means of the X-ray diagnostic device or another medical diagnostic system, such as a nuclear medicine measuring system, preferably prior to an operative intervention. During the operative intervention two-dimensional image information is measured by means of the X-ray diagnostic device and computationally overlaid by the three-dimensional image information. Owing to the additional spatial information an improved spatial orientation of a treating physician is achieved during the operative intervention.

Most notably in angiocardiography, medical diagnostic systems are employed today which combine the principle of the C-arm and the principle of the at least two X-ray measuring apparatuses. A medical diagnostic system of said type has two independently movable C-arms at the ends of which a measuring device is disposed in each case. The C-arms permit a virtually arbitrary positioning of the X-ray measuring apparatuses, with the result that a treating physician can study a region that is of interest for an assessment from two angles of view in each case. In particular when performing a medical intervention, such as when introducing a catheter, it is thus considerably easier for the treating physician to find his/her bearings when positioning said catheter. During the recording of the images there is a reduction in the need for a contrast agent and the time that the catheter remains in a blood vessel is also reduced, since two projection directions can be captured simultaneously based on a single injection. In addition, the assessment by means of two different image representations of one and the same bodily region makes it easier to diagnose a stenosis that may possibly be present.

A medical diagnostic system of said type also performs good service in neuroradiology in the repair of cerebral vessels. Cerebral vessels are embodied in a convoluted and irregular form, so here too, when introducing a catheter for the purpose of performing a medical intervention, studying a vessel from two different perspectives constitutes a valuable orientation aid for the treating physician.

SUMMARY OF THE INVENTION

The object underlying the invention is to specify a medical diagnostic system by means of which a treating physician can be furnished with additional information for developing a medical diagnosis or for performing a medical intervention.

Toward that end the medical diagnostic system has two C-arms which are adjustable with the aid of drive means and serve as retaining devices for one medical measuring system in each case. At least one evaluation unit and at least one display element are provided for each medical measuring system. The first measuring system is an X-ray measuring system having an X-ray emitter and an X-ray detector. The second measuring system is a nuclear medicine measuring system.

By means of the two adjustable C-arms it is possible to produce images of one and the same bodily region simultaneously both with the X-ray measuring system and with the nuclear medicine measuring system.

Thus, for example, a tumor can be particularly well recorded by means of the nuclear medicine measuring system. The X-ray measuring system, which provides a significantly better spatial resolution in the image representation, enables a medical intervention to be carried out on such a tumor, in particular in order to close the blood vessels supplying the tumor or to cauterize the tumor. The result of said medical intervention is immediately traceable using the nuclear medicine measuring system. It is thus no longer necessary to switch between an X-ray measuring system and a nuclear medicine measuring system, which switching often must even be done on different days due to the utilization to full capacity of the corresponding individual medical diagnostic systems in a clinic or a medical practice. A patient can consequently be treated very promptly. Furthermore, the iterative switching between an X-ray measuring system for the purpose of carrying out a medical intervention and a nuclear medicine measuring system for the purpose of monitoring said intervention is rendered superfluous. As a result medical interventions of this kind can be performed significantly more cost-effectively than is possible by the conventional treatment route using two medical diagnostic systems.

In addition the X-ray measuring system or the nuclear medicine measuring system can also be used in isolation, which means that henceforth possibly only one medical diagnostic system needs to be purchased, where formerly it would have been necessary to procure two medical diagnostic systems.

In one variant the nuclear medicine measuring system is a positron emission tomograph (PET) which comprises two scintillation detectors arranged one at each end of the second C-arm. In positron emission tomography a glucose solution, for example, is administered to a person that is to undergo examination prior to the examination, the glucose molecules of said solution being marked with a short-lived positron emitter. The radioactively marked glucose is incorporated in particular by somatic cells with an increased metabolic activity. These regions of increased metabolic activity very often represent an accumulation of cancer cells. Said regions of increased metabolic activity can be detected by means of a spatially resolved registration of positron decays, so recorded image information has a very important supporting function in tumor diagnostics. In contrast to the X-ray measuring system, however, the PET supplies very much less detailed anatomical information. The PET has a spatial unsharpness of several millimeters, which means that a detected tumor cannot be located accurately. The precise localization is performed rather by means of the X-ray measuring system, the images of which represent the tumor with significantly poorer contrast, yet with a significantly better spatial resolution.

In another variant the nuclear medicine measuring system is a single-photon emission computer tomograph (SPECT) which comprises one or two detectors disposed in each case at an end of the second C-arm. In this case, prior to an examination, a radionuclide, for example xenon, is administered to the patient. The gamma radiation emitted by said radionuclide penetrates different types of bodily tissue of the person in different ways and is registered by means of the single-photon emission computer tomograph. Tumors can also be detected by means of this nuclear medicine measuring method. The SPECT is cheaper than the PET, but has a lower spatial resolution, which means that it is necessary to consider in each case with regard to the configuration of the second C-arm of the medical diagnostic system whether costs are to be saved or a higher resolution is important.

If the nuclear medicine measuring system is a SPECT which comprises a detector disposed at one end of the second C-arm it is advantageous to provide the second end of the second C-arm with a counterweight. Said counterweight serves for mechanical stabilization. In this way the weight ratios of the second C-arm are comparable to those of the first C-arm, where both ends of the C-arm are also under load. By loading both ends of the second C-arm it can be achieved that the positioning of said second C-arm is carried out more precisely because of the mechanical stabilization.

In one development a control unit is configured in order to record a nuclear medicine diagnostic image from the same perspective for each X-ray medical diagnostic image. In a simultaneous measurement using the X-ray medical measuring system and using the nuclear medicine measuring system, the identical measurement positions are assumed with a time offset by means of both C-arms. In this way it is possible to obtain a corresponding nuclear medicine diagnostic image for each X-ray medical diagnostic image. Thus, on the one hand the high anatomical precision of the X-ray medical diagnostic images is available, while on the other hand the nuclear medicine diagnostic image enables tissue functions to be diagnosed, in particular tumors detected. The two diagnostic images can either be displayed on two display elements arranged side by side or else they are overlaid computationally such that the X-ray medical information and the nuclear medicine information are automatically combined in a single diagnostic image. The latter method in particular enables a treating physician to perform a medical intervention in a particularly targeted and rapid manner. In this way it is also ensured that the physical stress for a person remains within comparatively limited bounds.

In one development the control unit is embodied such that prior to a measurement of the diagnostic image by means of the X-ray detector of the X-ray measuring system, a dark image corresponding to the measurement position of the diagnostic image is recorded. In addition the evaluation unit is configured to store the dark image in an evaluation unit and to combine each diagnostic image with its corresponding dark image automatically in order to improve contrast. In this way account is taken of the fact that the radionuclides incorporated for the purpose of performing the PET or SPECT measuring method constantly emit radiation and consequently their gamma quanta also continuously strike the X-ray detector and lead to discolorations and hence distortions of the gray-scale image captured by means of the X-ray detector. This emission of X-ray quanta is not isotropic, but essentially constant over a relatively long period of time.

Thus, with the aid of a dark image it is possible to determine the percentage of X-ray quanta registered by the X-ray detector which does not originate from the X-ray source. Since this percentage remains largely constant over time, it is also registered by the X-ray detector in each case during the measurement by means of the X-ray measuring system and hence with the operation of the X-ray source. An automatic merging of a diagnostic image with its corresponding dark image therefore contributes toward improving contrast and ensures that the X-ray quanta originating from the radionuclides do not distort the diagnostic image and in consequence also falsify the medical diagnosis.

In one development the control unit is configured to move both C-arms simultaneously when recording a plurality of diagnostic images and to measure X-ray medical image information and nuclear medicine image information simultaneously. This enables the X-ray medical image information and the nuclear medicine image information to be captured in a single operation.

In another variant the control unit is configured to move the C-arms sequentially in time when recording a plurality of diagnostic images and to measure X-ray medical image information and nuclear medicine image information sequentially in time. In this way the former execution of a medical intervention can be performed as it were in a time lapse manner. First, X-ray medical image information and nuclear medicine image information are captured in sequence. Next, the medical intervention is carried out with the support of the anatomical information provided by the X-ray measuring system. In a further operation the result of said medical intervention is monitored by means of the nuclear medicine measuring system. If necessary a second medical intervention is performed, once again with the support of the X-ray medical measuring system, etc., etc.

The separate movement of the two C-arms also permits mutually independent operation of the two measuring systems. Accordingly, when solely recording X-ray medical image information the medical diagnostic system can also be used as a conventional X-ray measuring system with one C-arm.

A combined or separate movement of the two C-arms enables a plurality of diagnostic images to be recorded sequentially. Said recorded images can be automatically combined with one another in an evaluation unit, thereby producing three-dimensional image information. If three-dimensional image information of the same bodily region is acquired by means of both the X-ray medical imaging system and the nuclear medicine imaging system, the medical image information obtained is similar to that of medical diagnostic systems in which a computer tomograph is coupled in each case to a PET or a SPECT.

The object is further achieved by means of a method for capturing medical image information. In this case the advantages cited in relation to the medical diagnostic system for the preferred embodiments should also be applied to the claims directed to the method.

BRIEF DESCRIPTION OF THE DRAWINGS

An exemplary embodiment of the invention is explained in more detail below with reference to a drawing.

The single FIGURE shows a medical diagnostic system in a schematic representation.

DETAILED DESCRIPTION OF THE INVENTION

The medical diagnostic system 2 has a first C-arm 4 which is supported by a ceiling-mounted fixing 6 and is adjustable in adjustment direction 8. Said first C-arm 4 serves as a retaining device for an X-ray measuring system 10 which is composed of an X-ray emitter 12 at one end of the first C-arm 4 and a corresponding X-ray detector 14 at the other end of the first C-arm 4.

The medical diagnostic system 2 also has a second C-arm 16 which is supported by a floor-mounted fixing 18 and is adjustable in adjustment direction 20. Said second C-arm 16 serves as a retaining device for a nuclear medicine measuring system 22 which comprises a first scintillation detector 24 disposed at one end of the second C-arm 16 and a second scintillation detector 26 disposed at the other end of the second C-arm 16.

The positioning of a person (not shown in the FIGURE) is performed using a patient stretcher 28 which is supported and can be positioned by means of a support leverage system 30 of a supporting and positioning device 32 disposed on a ceiling.

A measurement position is set by means of a control unit 34. An adjuster system integrated in the ceiling-mounted fixing 6 and not shown in the FIGURE is controlled by means of a control signal S generated by the control unit 34, thereby enabling the first C-arm 4 to move in adjustment direction 8.

The second C-arm 16 is positioned by means of an adjuster system integrated in the floor-mounted fixing 18 and also not shown in the FIGURE in adjustment direction 20 under the control of a further control signal S generated by the control unit 34.

In addition, the patient stretcher 28 can be positioned by means of a third control signal S generated by the control unit 34 by way of a further adjuster system integrated in the supporting and positioning device 32.

Thus, practically any desired measurement position can easily be set.

The X-ray emitter 12 of the X-ray measuring system 10 generates X-ray quanta which locally irradiate a person to be examined. Said X-ray quanta are registered by the X-ray detector 14 and converted into X-ray medical image information B1. Said X-ray medical image information B1 is processed and edited by a first evaluation unit 36 and displayed as a grayscale image on a first display element 38 embodied as a monitor.

The first scintillation detector 24 and the second scintillation detector 26 of the nuclear medicine measuring system 22 register X-ray quanta which fly apart at an angle of 180° and indicate a positron decay occurring previously in time. The nuclear medicine image information B2 generated by the first scintillation detector 24 and the second scintillation detector 26 is converted into a false-color image by a second evaluation unit 40 and displayed on a second display element 42 embodied as a monitor.

The X-ray medical image information B1 and the nuclear medicine image information B2 are also automatically combined with one another in a third evaluation unit 44 and displayed as overlaid image information B1XB2 on a third display element 46 likewise embodied as a monitor.

Owing to the X-ray medical image information B1 and the nuclear medicine image information B2 it is possible for a treating physician on the one hand to clearly identify tumors on the basis of the nuclear medicine image information B2. Because of the high spatial resolution of the X-ray medical image information B2 a medical intervention, for example using a catheter, can be carried out immediately. For example, blood vessels supplying the tumor can be bonded together by means of the catheter and the tumor "starved", so to speak. The result of this medical intervention can be monitored immediately and by means of the same medical diagnostic system 2 on the display elements 38, 42 and 46. In this way it is possible to achieve a rapid treatment of a person.

Since the person to be treated was provided with a radionuclide prior to the examination, for example by means of infusion or via an ingestion, said person has incorporated the radionuclide. As this radionuclide is not deposited evenly throughout the body, the emission of the positron annihilation radiation is anisotropic. The X-ray quanta generated during the annihilation of the positrons not only strike the first scintillation detector 24 and the second scintillation detector 26, but also the X-ray detector 14. They are registered by the X-ray detector 14 as local intensity maxima. Since this annihilation process takes place continuously during the entire medical intervention, the X-ray medical image information B1 would be distorted as a result. To remedy this, the control unit 34 is configured to record a dark image D by means of the X-ray detector 14 prior to a measurement in a particular measurement position. The first evaluation unit 36 and the third evaluation unit 44 are configured to store said dark image D. X-ray medical image information B1 subsequently recorded in the same measurement position is automatically combined with this dark image D in the evaluation unit 36,44, and specifically in such a way that the image information measured by means of the dark image D is essentially subtracted from the X-ray medical image information B1. This reliably prevents the X-ray medical image information B1 being corrupted by X-ray quanta originating from a positron decay.

The invention claimed is:

1. A medical diagnostic system, comprising:
    an X-ray measuring system having an X-ray emitter and an X-ray detector that is arranged in a first C-arm and records an X-ray medical image of a patient; and
    a nuclear medicine measuring system that is arranged in a second C-arm and records a uclear medicine image of the patient,
    wherein the first and second C-arms are separate C-arms.

2. The medical diagnostic system as claimed in claim 1, wherein the X-ray medical image and the nuclear medicine image are recorded simultaneously or sequentially.

3. The medical diagnostic system as claimed in claim 1, wherein the X-ray emitter is disposed at one end and the X-ray detector is disposed at an opposite end of the first C-arm.

4. The medical diagnostic system as claimed in claim 1, wherein the nuclear medicine measuring system is a positron emission tomograph comprising two scintillation detectors that are respectively disposed at one end of the second C-arm.

5. The medical diagnostic system as claimed in claim 1, wherein the nuclear medicine measuring system is a single-photon emission computer tomograph comprising two detectors that are respectively disposed at one end of the second C-arm.

6. The medical diagnostic system as claimed in claim 1, wherein in a single-photon emission computer tomograph comprising a detector that is disposed at one end of the second C-arm and a counterweight that is disposed at another end of the second C-arm.

7. The medical diagnostic system as claimed in claim 1, further comprising a control unit that controls the nuclear medicine measuring system to record the nuclear medicine image from an identical perspective of the X-ray medical image.

8. The medical diagnostic system as claimed in claim 7, wherein the control unit controls the X-ray measuring system to record a dark image at a measurement position of the X-ray medical image before recording the X-ray medical image.

9. The medical diagnostic system as claimed in claim 8, wherein the dark image is stored in an evaluation unit and automatically combined with the X-ray medical image to improve a contrast of the X-ray medical image.

10. The medical diagnostic system as claimed in claim 7, wherein the control unit simultaneously moves the first and the second C-arms for simultaneously recording a plurality of X-ray medical images and nuclear medicine images of the patient.

11. The medical diagnostic system as claimed in claim 7, wherein the control unit sequentially moves the first and the second C-arms for sequentially recording a plurality of X-ray medical images and nuclear medicine images of the patient.

12. A method for capturing a medical image information of a patient, comprising:
    moving a first C-arm in a first direction;
    moving a second C-arm in a second direction;
    recording an X-ray medical image of the patient by an X-ray measuring system that is arranged in a first C-arm;
    recording a nuclear medicine image of the patient by a nuclear medicine measuring system that is arranged in a second C-arm; and
    converting the X-ray medical image and the nuclear medicine image into a diagnostic image for diagnosing the patient,
wherein the first and second C-arms are separate C-arms.

13. The method as claimed in claim 12, wherein the X-ray medical image and the nuclear medicine image are recorded simultaneously or sequentially.

14. The method as claimed in claim 12, wherein the nuclear medicine image is recorded from an identical perspective of the X-ray medical image.

15. The method as claimed in claim 12, wherein a dark image is recorded by the X-ray measuring system at a measurement position of the X-ray medical image before recording the X-ray medical image.

16. The method as claimed in claim 15, wherein the dark image is stored and automatically combined with the X-ray medical image to improve a contrast of the X-ray medical image.

17. The method as claimed in claim 12, wherein the first and the second C-arms are moved sequentially for sequentially recording a plurality of X-ray medical images and nuclear medicine images of the patient.

18. The method as claimed in claim 12, wherein the first and the second C-arms are moved sequentially for sequentially recording a plurality of X-ray medical images and nuclear medicine images of the patient.

19. The medical diagnostic system as claimed in claim 1, wherein the first C-arm and the second C-arm have different axes of rotation.

20. The method as claimed in claim 12, wherein the first C-arm and the second C-arm have different axes of rotation.

\* \* \* \* \*